US012734302B2

(12) United States Patent
Nadadur

(10) Patent No.: US 12,734,302 B2
(45) Date of Patent: Sep. 15, 2026

(54) EXCESS DOSE ALERT SYSTEM FOR A DOSING PEN

(71) Applicant: DelPharma LLC, Staten Island, NY (US)

(72) Inventor: Sandhya Nadadur, Staten Island, NY (US)

(73) Assignee: DELPHARMA LLC, Staten Island, NY (US)

( * ) Notice: Subject to any disclaimer, the term of this patent is extended or adjusted under 35 U.S.C. 154(b) by 448 days.

(21) Appl. No.: 18/370,609

(22) Filed: Sep. 20, 2023

(65) Prior Publication Data

US 2025/0090761 A1 Mar. 20, 2025

(51) Int. Cl.

| | |
|---|---|
| ***A61M 5/315*** | (2006.01) |
| ***A61M 5/31*** | (2006.01) |
| ***A61M 5/32*** | (2006.01) |

(52) U.S. Cl.

CPC ........ *A61M 5/3155* (2013.01); *A61M 5/3129* (2013.01); *A61M 5/3158* (2013.01); *A61M 5/32* (2013.01); *A61M 2202/0486* (2013.01)

(58) Field of Classification Search

CPC ............ A61M 5/31535; A61M 5/3155; A61M 5/31551; A61M 5/31553; A61M 5/31566; A61M 5/3157; A61M 5/3158; A61M 5/31593; A61M 2205/18; A61M 2205/183; A61M 2205/186; A61M 2205/581; A61M 2205/582; A61M 2205/583

See application file for complete search history.

(56) References Cited

U.S. PATENT DOCUMENTS

| | | | | |
|---|---|---|---|---|
| 9,011,391 | B2 | 4/2015 | Veasey | |
| 11,424,026 | B2 * | 8/2022 | Groeschke ........ | A61M 5/31533 |
| 2011/0270222 | A1 | 11/2011 | Wei | |
| 2016/0012205 | A1 * | 1/2016 | Saint ........................ | H04B 7/24 604/189 |
| 2016/0296716 | A1 * | 10/2016 | Cabiri ................. | A61M 5/5086 |
| 2019/0175841 | A1 * | 6/2019 | Sjolund ................ | A61B 5/0004 |

(Continued)

OTHER PUBLICATIONS

Wockhardt, Dispo Pen and Pen Royale, accessible at <https://www.ide.uk.com/medical/case-studies/dispo-pen-and-pen-royale/><accessed on Jul. 23, 2023>.

(Continued)

*Primary Examiner* — Kami A Bosworth
(74) *Attorney, Agent, or Firm* — CRGO Global; Steven M. Greenberg

(57) ABSTRACT

A dosing pen includes a barrel housing a reservoir of fluid and coupled to a piston plunger longitudinally movable within the reservoir. A needle assembly fits to a distal end of the barrel providing a channel for the fluid to exit an orifice of a needle in the assembly. A dosage knob calibrates a volume of the fluid to be forced through the needle upon the actuation of the plunger. As well, an injection button, upon depression, motivates the plunger towards the assembly. A feedback element fixed to the dosing pen has dual states of an operable state initiated in response to the depression of the button and for a period of time measured by a countdown timer triggered by the depression, and an inoperable state otherwise. Finally, a finger placement sensor at a top surface of the button electrically actuates the feedback element when latched in the operable state.

8 Claims, 2 Drawing Sheets

(56) References Cited

U.S. PATENT DOCUMENTS

2021/0060260 A1* 3/2021 Ruiz-Valdepeñas Martin De Almagro ........... A61M 5/31551
2024/0252757 A1* 8/2024 Bruegger ............ A61M 5/3146

OTHER PUBLICATIONS

Novo Nordisk Inc., NovoPen 3 PenMate Instruction Manual (May 17, 2005).

* cited by examiner

EXCESS DOSE ALERT SYSTEM FOR A DOSING PEN

BACKGROUND OF THE INVENTION

Field of the Invention

The present invention relates to the field of syringes and dosing pens and more particularly to an indicator of dosing in a syringe or dosing pen.

Description of the Related Art

A dosing pen is a medicine delivery system akin to a syringe but providing the ability to precisely specify a volume of dose and a repeatable number of doses. Traditional dosing pens accept cartridges of medicine so that the pen can be reused, though some dosing pens can be disposable after the doses of the pen have been dispensed. The architecture of the dosing pen includes a pen body and pen cap, the pen body including a barrel, reservoir, needle assembly, dosage selector and dosing button. In operation, the depressing of the dosing button actuates a plunger within the barrel longitudinally driving the plunger towards a rubber stopper in a cartridge in the reservoir so as to force the fluid in the reservoir out of the reservoir, through a needle fixed to the needle assembly and transdermally into the patient.

Notably, the volume of fluid delivered for each dose can be selected by a dosage selector which acts to limit the longitudinal motion of the plunger responsive to the depressing of the dosing button so as to correspondingly limit the amount of fluid delivered in the dose through the needle assembly. However, once the dose has been delivered, in a multi-dose pen it is difficult to confirm that the dose has been delivered after a lapsing of time. Thus, it is common for the end user to accidentally deliver double doses within a set time period having forgotten about the initial dose.

In some instances, double dosing is of no consequence, but in many instances, delivering a double dose can be life threatening.

BRIEF SUMMARY OF THE INVENTION

Embodiments of the present invention address deficiencies of the art in respect to avoiding excess dosing with a dosing pen and provide a novel and non-obvious dosing pen structured to detect an attempt to deliver an excess dose of fluid and to alert the user of the attempt to deliver the excess dose. In an embodiment of the invention, the dosing pen includes a barrel adapted to house a fluid reservoir of fluid such as insulin, and coupled to a piston plunger configured for longitudinal movement within the fluid reservoir. The dosing pen additionally includes a needle assembly fit to a distal end of the barrel and providing a channel for the fluid in the reservoir to an exit orifice of a needle in the needle assembly.

The dosing pen further includes a dosage knob calibrating a volume of the fluid to be forced through the needle upon the longitudinal actuation of the piston plunger. The dosing pen yet further includes an injection button configured upon depression to motivate the piston plunger towards the needle assembly. The dosing pen even yet further includes a feedback element fixed to the dosing pen and having dual states consisting of an operable state initiated in response to the depression of the injection button and for a period of time measured by a countdown timer triggered by the depression, and an inoperable state otherwise. Finally, the dosing pen includes a finger placement sensor at a top surface of the button, the sensor electrically actuating the feedback element when the feedback element has been latched in the operable state.

In one aspect of the embodiment, a contact sensor is disposed on the dosage knob coupled to a microelectronic state machine that drives the dual states of the feedback element. In this regard, the contact sensor advances the state machine upon a breaking of electrical contact when the dosage knob moves from an initial position to a dose position. As well, the contact sensor again advances the state machine upon a restoration of the electrical contact responsive to a return of the dosage knob to the initial position. As such, an output of the state machine both activates the countdown timer and places the feedback element into the operable state for the period of time indicating the depression of the injection button.

Other aspects of the dosing pen include the following features which may be included individually or in different combinations as follows:

- The feedback element is a light emitting diode (LED).
- The feedback element is a piezoelectric speaker.
- The feedback element is a piezoelectric vibrator.
- The countdown timer is tunable to provide for different discrete durations for the period of time, for instance four hours, eight hours, twelve hours and twenty-four hours.
- The finger placement sensor comprises a dual actuator of a photovoltaic sensor and capacitive touch sensor.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for a dosing pen adapted to alert the user of an attempt to inject an excess does of fluid from the pen. In accordance with an embodiment of the invention, a dosing pen is equipped with a feedback element configured to detect an attempt to deliver an excess dose of fluid from the pen within a threshold period of time. The feedback element responds to an attempt to depress an injection button of the dosing pen within a threshold period of time of the injection button having been previously depressed thereby indicating the excess dose. To that end, the feedback element has dual states which are triggered by the depressing of the injection button and which states include an operable state initiated in response to the depression of the injection button and for a period of time measured by a countdown timer triggered by the depression, and an inoperable state otherwise, so that a finger placement sensor at a top surface of the button electrically actuates the feedback element when the feedback element has been latched in the operable state.

Figure 1:
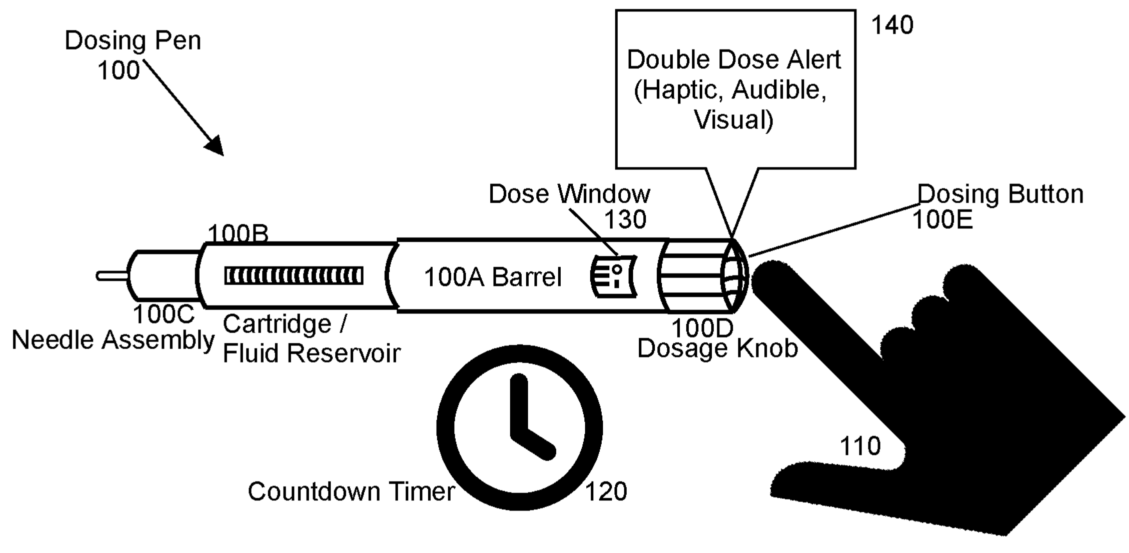
FIG. 1 is a perspective view of a dosing pen adapted to alert the end user of an attempt to inject an excess dose of fluid from the pen.

In further illustration, FIG. 1 is a perspective view of a dosing pen adapted to alert the end user of an attempt to inject an excess dose of fluid from the pen. As shown in FIG. 1, a dosing pen 100 includes a barrel 100A coupled to a cartridge/fluid reservoir 100B further coupled to a needle assembly 100C. The cartridge/fluid reservoir 100B encapsulates therein fluid such as insulin to be transdermally dispensed from the needle assembly 100C caused by the actuation of a plunger assembly (not shown) encapsulated within the barrel 100A by means of a depressing of a dosing button 100E with a finger 110. Dosage knob 100D at an end of the barrel 100A opposite the cartridge/fluid reservoir 100B establishes a maximum amount of the fluid in the cartridge/fluid reservoir 100B dispensed through the needle assembly 100C based upon a rotation of the dosage knob 100D to indicate a desired dosage in the dose window 130.

Notably, upon delivering a dose through the needle assembly 100C, a countdown timer 120 included as part of an electronics package (not shown) within the dosing pen 100 initiates activating a sensor within the dosing button 100E. During a period of time defined by the countdown timer 120, should the sensor sense the touching of the dosing button 100E in an attempt to administer a subsequent dose, the electronics package within the dosing pen 100 generates an alert 140, such as a visual illumination of a light emitting diode (LED), an audible tone through a piezoelectric speaker, or haptic feedback through a piezoelectric vibrator. In this way, double dosing is avoided during the period defined by the countdown timer.

Figure 2:
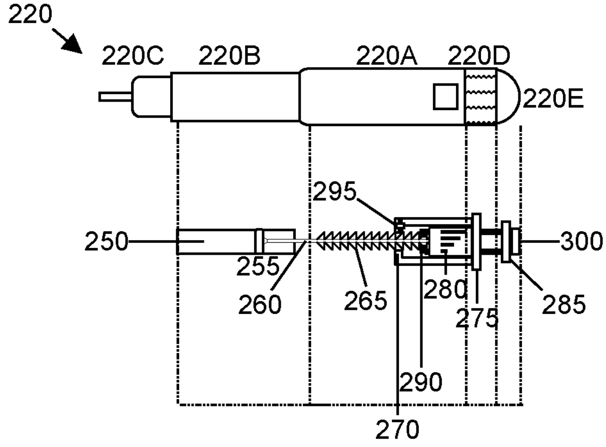
FIG. 2 is a schematic illustration of the dosing pen of FIG. 1.

In further illustration of the structure of the dosing pen 100 of FIG. 1, FIG. 2 is a schematic illustration of the dosing pen of FIG. 1. In this regard, a dosing pen 220 includes a barrel 220A coupled to a cartridge/fluid reservoir 220B which is further coupled to a needle assembly 220C. Opposite to the cartridge/fluid reservoir 220B and coupled to the barrel 220A, a dosage knob 220D is adapted for rotational movement about the barrel 220A. Finally, a dosing button 220E is fixed at a proximal end of the dosage knob 220D opposite the barrel 220A.

As can be seen, disposed within the dosage knob 220D, a dose assembly 275 includes at least one arm 270 extending longitudinally along an interior portion of the barrel 220A culminating in an inward ledge 270. Though not shown in the illustration, an exterior surface of the dose assembly is threaded and mates with threads defined on an interior surface of the barrel 220A so as to cause the dose assembly 275 to longitudinally move towards the distal end of the barrel 220A proximate to the cartridge/fluid reservoir 220B responsive to a rotation of the dosing knob 220D connected to the dose assembly 275. Dose indicator markings 280 defined on the exterior surface of the dose assembly 275 provide a visual indication of a dose setting determined by a positioning of the dose assembly 275 within the barrel 220A.

The dose assembly 275 envelops a plunger 260 positioned through an interior channel of the dose assembly 275. The plunger 260 at a distal end contacts a rubber stopper 255 disposed within a fluid chamber 250 of the cartridge/fluid reservoir 220B so as to cause fluid within the fluid chamber 250 to exit the chamber into the needle assembly 220C as the rubber stopper 225 is driven longitudinally towards the needle assembly 220C by the longitudinal movement of the plunger 260. The plunger 260 is caused to move longitudinally by activation of the dosing button assembly 285 which includes at a proximal end a pressing surface and at a distal end, one or more pawls 290.

In so far as the surface of the plunger 260 includes a ratchet track of teeth 265, the pawl 290 in contacting the teeth 265 drive the plunger 260 longitudinally towards the rubber stop 255 when the pressing surface is pressed, but a spring return causes the pressing surface to retract with the pawls 290 along the sloping portions of the teeth 265 permitting the opposite longitudinal movement of the dosing button assembly 285 without also causing the opposite longitudinal movement of the plunger 260. The longitudinal movement of the plunger 260 coupled to the dosing button assembly 285 by the contact of the perpendicular portion of the teeth 265 with the pawls 290 is limited, however, by the inward ledge 270 positioned at a desired location within the barrel 220 by operation of the dose assembly 275 and contacting the pawls 290.

Importantly, an electronics package 300 is included in the dosing pen 220, for instance within an interior portion of the dosing button 220E. The electronics package 300 includes a contact sensor 295 at the inward ledge 270 sensing contact between the pawls 290 and the inward ledge 270, a touch sensor such as a photovoltaic sensor or a capacitive touch sensor (not shown) sensing a touching of the dosing button 220E with a finger, and a feedback element (not shown) such as an LED, piezoelectric speaker or piezoelectric vibrator. The electronics package 300 further can include supporting structural elements as shown in FIG. 3.

Figure 3:
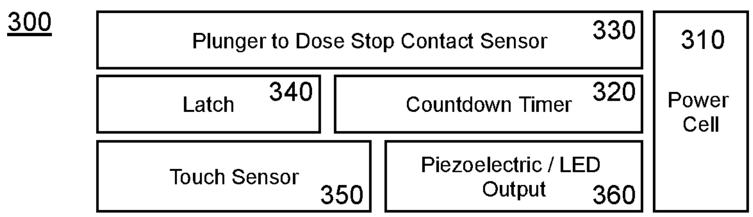
FIG. 3 is a block diagram of an electronics package adapted to perform the alerting of FIG. 1; and, FIG. 4 is a flow chart illustrating a process of generating an alert of an attempt to inject an excess dose of fluid from the pen of FIG. 1 performed by the electronics package of FIG. 3.

To that end, FIG. 3 is a block diagram of an electronics package adapted to perform the alerting of FIG. 1. The electronics package 300 includes a contact sensor 330 adapted to detect when a dose has been delivered through the needle assembly of the dosing pen, for instance an optical or mechanical or electrical contact sensor detecting a contacting of a dosing button assembly with the dose assembly. The electronics package 300 further includes a countdown timer 320 adapted to countdown a pre-determined duration of time upon activation concurrent with the setting of a latch 340 and resetting the latch subsequent to the duration of time, a touch sensor 350 sensing a touching of the dose button of the dosing pen and activating a piezoelectric or LED output element 360 subject to the setting of the latch 340, and a power cell 310 powering the components of the electronics package 300.

Optionally, the electronics package 300 can include a micro-controller (not shown) powered by the power cell 310 and coupled to an LED display (not shown) fixed to an exterior surface of the dosing pen. The micro-controller can include embedded program instructions adapted to capture a timestamp from an internal clock responsive to the setting of the latch 340 and to store the timestamp in a memory element of the microcontroller. The embedded program instructions of the micro-controller additionally can be adapted to convert the timestamp to a 12 hour or 24 hour time value and to display the time value in the LED display responsive to the touch sensor sensor 350 sensing the touching of the dose button of the dosing pen. In this way, upon detecting a possible attempt to double dose, the dosing pen can indicate a last time when the dose had been delivered.

Figure 4:
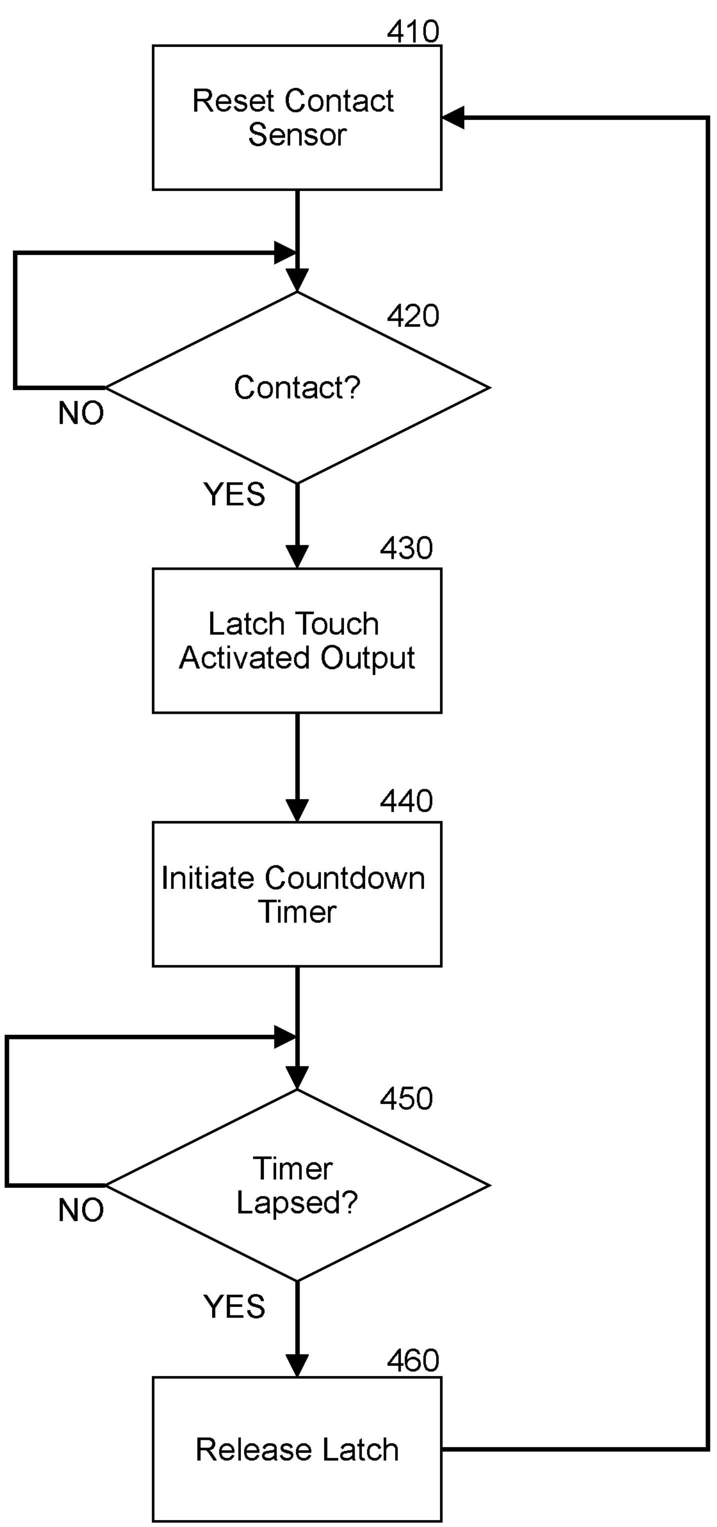

In yet further illustration of the operation of the electronics package 300, FIG. 4 is a flow chart illustrating a process of generating an alert of an attempt to inject an excess dose of fluid from the pen of FIG. 1 performed by the electronics package of FIG. 3. As shown in FIG. 4, initially, the contact sensor 410 resets and awaits detection of a contacting of the dosing button assembly with the dose assembly. In decision block 420, it is determined if the dose assembly has been contacted by the dosing button assembly. If so, in block 430 the latch is activated permitting the generation of an alert responsive to a touching of the dose button. Concurrently, in block 440, a countdown timer is initiated for a predetermined amount of time which may be variably established, for instance at four hour, eight hour, twelve hours and twenty-four hour intervals. In decision block 450, it is determined if the timer has lapsed. If not, the latch remains active. But otherwise, in block 460 the latch is released thereby inhibiting the generation of an alert responsive to the touching of the dose button.

The terminology used herein is for the purpose of describing particular embodiments only and is not intended to be limiting of the invention. As used herein, the singular forms “a”, “an” and “the” are intended to include the plural forms as well, unless the context clearly indicates otherwise. It will be further understood that the terms “include”, “includes”, and/or “including,” when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

I claim:

1. A dosing pen comprising:

a barrel adapted to house a fluid reservoir coupled to a piston plunger configured for longitudinal movement within the fluid reservoir;

a needle assembly fit to a distal end of the barrel and providing a channel for fluid in the fluid reservoir to travel to an exit orifice of a needle in the needle assembly;

a dosage knob calibrating a volume of the fluid to be forced through the needle upon longitudinal actuation of the piston plunger;

an injection button configured upon depression to motivate the piston plunger towards the needle assembly;

a feedback element having dual states consisting of an operable state and an inoperable state, the operable state initiated in response to the depression of the injection button and lasting for a period of time measured by a countdown timer triggered by the depression; and, a finger placement sensor at a top surface of the injection button, the sensor electrically actuating the feedback element when the feedback element has been latched in the operable state.

2. The dosing pen of claim 1, further comprising a contact sensor disposed on the dosage knob and coupled to a microelectronic state machine driving the dual states of the feedback element, the contact sensor advancing the state machine upon a breaking of electrical contact when the dosage knob moves from an initial position to a dose position, the contact sensor again advancing the state machine upon a restoration of the electrical contact responsive to a return of the dosage knob to the initial position, an output of the state machine both activating the countdown timer and placing the feedback element into the operable state for the period of time indicating the depression of the injection button.

3. The dosing pen of claim 1, wherein the feedback element is a light emitting diode (LED).

4. The dosing pen of claim 1, wherein the feedback element is a piezoelectric speaker.

5. The dosing pen of claim 1, wherein the feedback element is a piezoelectric vibrator.

6. The dosing pen of claim 1, wherein the countdown timer is tunable to provide for different discrete durations for the period of time selected from the group consisting of four hours, eight hours, twelve hours and twenty-four hours.

7. The dosing pen of claim 1, wherein the finger placement sensor comprises a dual actuator of a photovoltaic sensor and a capacitive touch sensor.

8. The dosing pen of claim 1, wherein the fluid is insulin.

* * * * *